United States Patent
Ronk

[11] Patent Number: 5,951,160
[45] Date of Patent: Sep. 14, 1999

[54] METHOD AND APPARATUS FOR PACKAGING, MIXING AND DELIVERING BONE CEMENT

[75] Inventor: Robert Ronk, Leesburg, Ind.

[73] Assignee: Biomet, Inc., Warsaw, Ind.

[21] Appl. No.: 08/975,023

[22] Filed: Nov. 20, 1997

[51] Int. Cl.⁶ ....................................................... B01F 15/02
[52] U.S. Cl. .................... 366/130; 366/182.2; 366/182.3
[58] Field of Search .................................... 366/139, 130, 366/150.1, 182.1, 182.3, 182.4; 206/220, 219, 221

[56] References Cited

U.S. PATENT DOCUMENTS

| | | |
|---|---|---|
| 1,387,839 | 8/1921 | Davis . |
| 2,477,598 | 8/1949 | Hain . |
| 2,605,896 | 8/1952 | Rohdin . |
| 2,690,179 | 9/1954 | Fox . |
| 2,724,383 | 11/1955 | Lockhart . |
| 2,726,656 | 12/1955 | Lockhart . |
| 2,750,719 | 6/1956 | Wandelt . |
| 2,756,874 | 7/1956 | Erickson et al. . |
| 2,756,875 | 7/1956 | Yochim . |
| 2,798,488 | 7/1957 | Hall . |
| 2,874,830 | 2/1959 | Birmingham, Jr. . |
| 2,893,547 | 7/1959 | Earl et al. . |
| 2,932,385 | 4/1960 | Bollmeier et al. . |
| 2,971,851 | 2/1961 | Kurtz . |
| 3,010,705 | 11/1961 | Brown . |
| 3,028,000 | 4/1962 | Clements et al. . |
| 3,077,262 | 2/1963 | Gaste . |
| 3,082,867 | 3/1963 | Gelpey . |
| 3,156,352 | 11/1964 | Hayhurst . |
| 3,190,619 | 6/1965 | Penney et al. . |
| 3,294,227 | 12/1966 | Schneider et al. . |
| 3,462,070 | 8/1969 | Corella . |
| 3,523,607 | 8/1970 | Gillemot et al. . |
| 3,556,290 | 1/1971 | Popkin-Clurman . |
| 3,608,709 | 9/1971 | Pike . |
| 3,618,283 | 11/1971 | Moore et al. . |
| 3,700,215 | 10/1972 | Hardman et al. . |
| 3,741,381 | 6/1973 | Thompson et al. . |
| 3,802,919 | 4/1974 | Saffir . |
| 3,809,224 | 5/1974 | Greenwood . |
| 3,847,279 | 11/1974 | Montgomery . |
| 3,964,604 | 6/1976 | Prenntzell . |
| 3,983,994 | 10/1976 | Wyslotsky . |

(List continued on next page.)

FOREIGN PATENT DOCUMENTS

| | | |
|---|---|---|
| 0 238 133 | 9/1987 | European Pat. Off. . |
| 0 434 105 A1 | 6/1991 | European Pat. Off. . |
| 0 495 155 A1 | 7/1992 | European Pat. Off. . |
| 1054170 | 9/1954 | France . |
| 1258379 | 3/1961 | France . |
| 26 02 282 A1 | 8/1976 | Germany . |
| 26 08 690 A1 | 9/1977 | Germany . |
| 27 27 451 A1 | 1/1979 | Germany . |
| 26 49 772 B2 | 2/1979 | Germany . |
| 697723 | 9/1953 | United Kingdom . |
| WO 84/03830 | 4/1984 | WIPO . |
| WO 86/06618 | 11/1986 | WIPO . |
| WO 90/13355 | 11/1990 | WIPO . |
| WO 96/36526 | 11/1996 | WIPO . |
| WO 96/36562 | 11/1996 | WIPO . |
| WO 97/18031 | 5/1997 | WIPO . |
| WO 97/46202 | 12/1997 | WIPO . |
| WO 98/20939 | 5/1998 | WIPO . |

*Primary Examiner*—Tony G. Soohoo
*Attorney, Agent, or Firm*—Harness, Dickey & Pierce, P.L.C.

[57] ABSTRACT

A method and apparatus for packaging, mixing and delivering bone cement formed from at least a first component and a second component includes a first container, a second container and a mixing member. The first container is operable to be selectively opened and closed and further operable to be sealably prepackaged with the first component of the bone cement. The second container is operable to deliver the second component of the bone cement to the first container. The mixing member forms a part of the first container and is operable to mix the first and second components of the bone cement substantially within only the first container.

9 Claims, 4 Drawing Sheets

U.S. PATENT DOCUMENTS

| | | |
|---|---|---|
| 4,000,996 | 1/1977 | Jordan . |
| 4,023,675 | 5/1977 | Claasen . |
| 4,039,076 | 8/1977 | Desaules . |
| 4,060,082 | 11/1977 | Lindberg et al. . |
| 4,277,184 | 7/1981 | Solomon . |
| 4,340,056 | 7/1982 | Erb . |
| 4,401,214 | 8/1983 | Kleckers . |
| 4,402,402 | 9/1983 | Pike . |
| 4,458,811 | 7/1984 | Wilkinson . |
| 4,462,224 | 7/1984 | Dunshee et al. . |
| 4,463,875 | 8/1984 | Tepic . |
| 4,469,153 | 9/1984 | Morrisette . |
| 4,551,135 | 11/1985 | Gorman et al. . |
| 4,608,043 | 8/1986 | Larkin . |
| 4,632,244 | 12/1986 | Landau . |
| 4,664,257 | 5/1987 | Nilson . |
| 4,721,390 | 1/1988 | Lidgren . |
| 4,743,229 | 5/1988 | Chu . |
| 4,795,265 | 1/1989 | Dahlberg et al. . |
| 4,798,288 | 1/1989 | Holzner . |
| 4,811,549 | 3/1989 | Usami et al. . |
| 4,878,903 | 11/1989 | Mueller . |
| 4,910,259 | 3/1990 | Kindt-Larsen et al. . |
| 4,927,012 | 5/1990 | Rowe . |
| 4,952,068 | 8/1990 | Flint . |
| 4,961,495 | 10/1990 | Yoshida et al. . |
| 4,973,168 | 11/1990 | Chan . |
| 4,994,029 | 2/1991 | Rohrbough . |
| 4,994,056 | 2/1991 | Ikeda . |
| 5,069,773 | 12/1991 | Frangioni . |
| 5,114,240 | 5/1992 | Kindt-Larsen et al. . |
| 5,121,302 | 6/1992 | Bay et al. . |
| 5,149,368 | 9/1992 | Liu et al. . |
| 5,226,877 | 7/1993 | Epstein . |
| 5,257,985 | 11/1993 | Puhl . |
| 5,257,986 | 11/1993 | Herbert et al. . |
| 5,281,265 | 1/1994 | Liu . |
| 5,322,161 | 6/1994 | Shichman et al. . |
| 5,385,546 | 1/1995 | Kriesel et al. . |
| 5,398,483 | 3/1995 | Smith et al. . |
| 5,425,580 | 6/1995 | Beller . |
| 5,549,380 | 8/1996 | Lidgren et al. ............... 366/139 |
| 5,588,745 | 12/1996 | Tanaka et al. . |

METHOD AND APPARATUS FOR PACKAGING, MIXING AND DELIVERING BONE CEMENT

BACKGROUND OF THE INVENTION

1. Field of the Invention

This invention relates generally to a method and apparatus for packaging, mixing and delivering bone cement and, more particularly, to a method and apparatus for mixing at least two or more components of the bone cement and delivering the bone cement to a desired surgical site in a convenient manner.

2. Discussion of the Related Art

The natural joints of the body often undergo degenerative changes due to a variety of etiologies. When these degenerative changes become so far advanced and irreversible, it may ultimately become necessary to replace a damaged joint with a prosthetic device. When such replacement becomes necessary, the prosthetic device that is implanted into the body is often secured to the natural bone by use of bone cement.

Other uses of bone cement include repairing or mending bone fractures or shattering of bone that may occur from extreme trauma. Bone cement may also be used for cosmetic or dental surgery as well. Moreover, bone cement may be used as a drug delivery or release system, whereby the bone cement is mixed with antibiotics or other desired drugs and applied to a specific surgical site such that the drugs leach out and are delivered directly to the surgical site. Some bone cements are also resorbable such that the bone cement is resorbed by the body over time.

When referring to bone cement herein, it will be understood that bone cement includes any type of surgical cement used with any type of surgical procedure including resorbable bone cement, bone graft material, bone substitute, bone filler, grouting material, morselized bone graft material, any other biologically compatible mixture which requires at least two or more components, or the bone cements set forth in U.S. Pat. No. 5,149,368 to Liu et al., U.S. Pat. No. 5,281,265 to Liu and U.S. Pat. No. 5,676,976 to Lee, all of which are hereby incorporated by reference.

The above-identified bone cement is generally a two-part material, one being a powder and the other being a liquid which requires the bone cement to be mixed prior to use. One method of mixing these products involves measuring and pouring each component into a bowl and mixing the components with a spatula or other mixing device. This technique is, however, also messy, inconvenient and may create voids or air pockets within the mixture. This technique also may lead to contamination of the bone cement during the mixing process and is very time consuming. As a result, surgical time and cost is generally increased. Moreover, bone cement generally has a specific setup time which also puts a further constraint on the surgeon to mix and deliver the bone cement to the surgical site in a timely manner. Still further, preparation of some bone cements yield offensive vapors. These vapors generally must be evacuated during the mixing, thus adding an additional step or process to the preparation of the bone cement. Still even further, in order to apply the bone cement to the desired surgical site, the bone cement is generally removed from the mixing bowl and delivered to a separate delivery system thereby potentially wasting and contaminating the bone cement, and further increasing the surgical time and cost.

What is needed then is a method and apparatus for packaging, mixing and delivering bone cement which does not suffer from the above mentioned disadvantages. This in turn, will reduce the overall surgical time, decrease surgical cost, reduce the potential for contamination of the bone cement, reduce or eliminate offensive vapors, provide a prepackaged mixing and delivery system which is convenient to use, provide a delivery system that is easily or automatically filled and provide a delivery system which requires a smaller incision to deliver the bone cement to the surgical site. It is, therefore, an object of the present invention to provide such a method and apparatus for packaging, mixing and delivering bone cement.

SUMMARY OF THE INVENTION

In accordance with the teachings of the present invention, a method and apparatus for packaging, mixing and delivering bone cement is disclosed. This is basically achieved by providing a first container which is prepackaged with the first component of the bone cement; opening the first container and delivering the second component of the bone cement to the first container; and mixing the first and second components to form the bone cement.

In one preferred embodiment, an apparatus for packaging, mixing and delivering bone cement formed from at least a first component and a second component includes a first container operable to be selectively opened and closed. The first container is further operable to be sealably prepackaged with the first component of the bone cement. The apparatus further includes a second container operable to deliver the second component of the bone cement to the first container. A mixing member forms a part of the first container and is operable to mix the first component and the second component of the bone cement substantially within only the first container.

Use of the present invention provides a method and apparatus for packaging, mixing and delivering bone cement from at least a first and a second component in a convenient manner. As a result, the aforementioned disadvantages associated with currently available methods and apparatus for mixing bone cement have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments of a method and apparatus for packaging, mixing and delivering bone cement are merely exemplary in nature and are in no way intended to limit the invention or its application or uses. Moreover, while the present invention is described in detail below with reference to a two-part bone cement, it will be appreciated by those skilled in the art that the present invention is clearly not limited to only a two-part bone cement as defined above but may also be used with any other materials which require at least two components to be mixed together before the material may be used.

Figures 1, 2, 3:
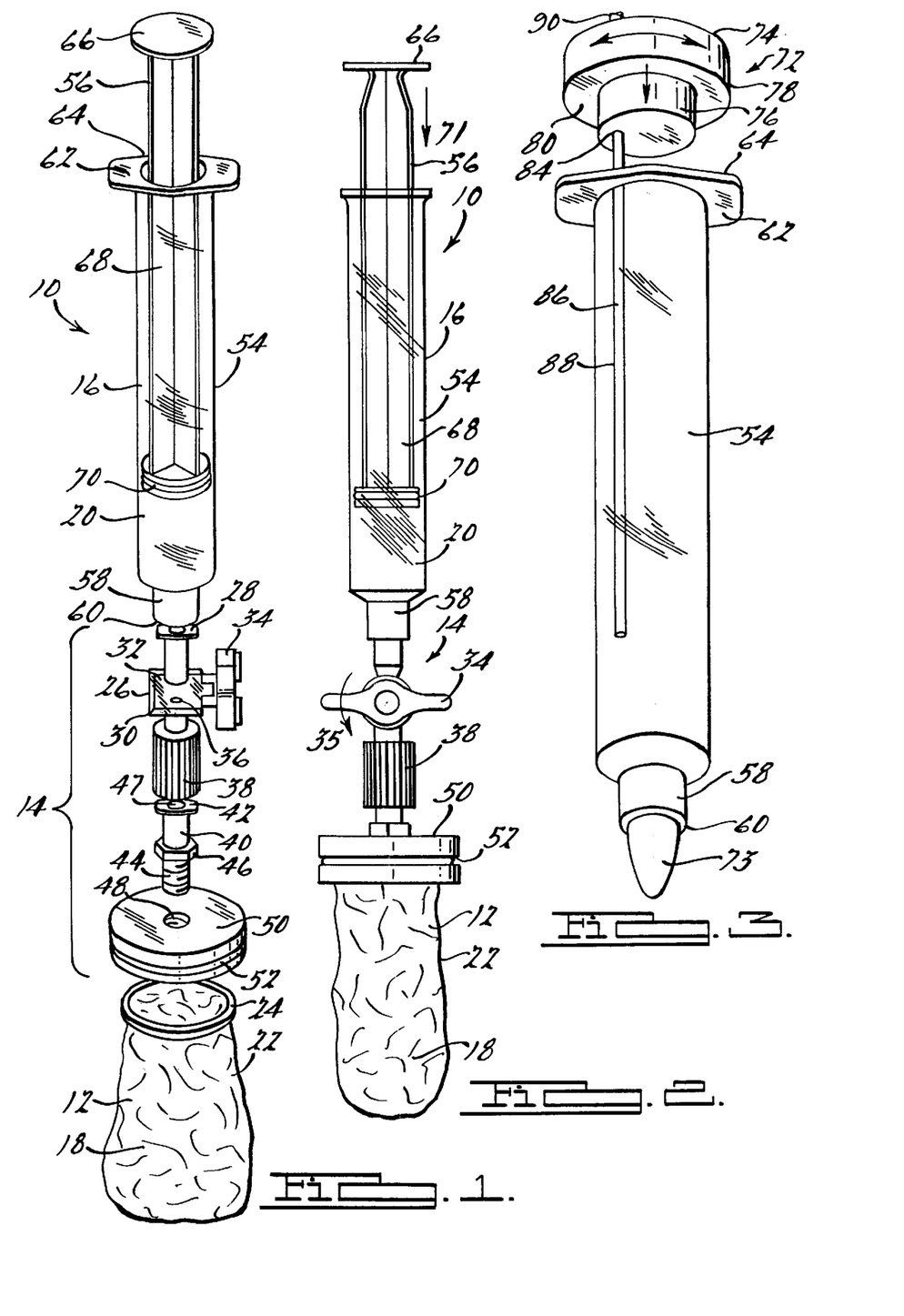
FIG. 1 is an exploded perspective view of an apparatus for packaging, mixing and delivering bone cement according to the teachings of a first preferred embodiment of the present invention.
FIG. 2 is an assembled side view of the apparatus shown in FIG. 1.
FIG. 3 is an exploded perspective view of an apparatus for packaging, mixing and delivering bone cement according to the teachings of a second preferred embodiment of the present invention.

Referring to FIGS. 1–2, an apparatus 10 for packaging, mixing and delivering bone cement formed from at least a first component and a second component is shown. The apparatus 10 includes a first container 12, a closure mechanism or barrier 14 and a second container 16. The first container 12 is preferably prepackaged with a first component 18 of the bone cement and the second container 16 is preferably prepackaged with a second component 20 of the bone cement. The first component 18 is preferably a powder component and the second component 20 is preferably a liquid component, such as that disclosed in the examples of U.S. Pat. No. 5,281,265 to Liu. The bone cement may also be formed from any other appropriate material.

The first container 12 is preferably a flexible and resilient bag or finger cot 12 such as a VWR Scientific Part No. 56613-417 or any other suitable flexible container 12 that may be sterilized, such as by gamma radiation. The first container 12 is defined by a flexible and resilient sidewall 22 and resilient lip 24 formed by rolling a portion of the sidewall 22. The closure mechanism 14 includes a valve mechanism or stopcock 26 which is selectively coupled to the second container 16, via a female Luer fitting 28. The valve mechanism 26 includes a valve body 30, a closure member 32 and a handle 34 coupled to the closure member 32. Upon rotating the handle 34 in a first counterclockwise direction, identified by arrow 35, the closure member 32 rotates within the valve body 30 to align a passage 36 axially along the valve body 30 and open the valve mechanism 26. Upon rotating the handle 34 in a second clockwise direction, the passage 36 in the closure member 34 is brought out of alignment to close the valve mechanism 26. The valve mechanism 26 is preferably a Cole-Parmer Part No. 30600-00. However, those skilled in the art will recognize that various other valve or closure mechanisms may also be used.

The valve mechanism 26 further includes a male Luer fitting 38 which is selectively coupled to a male Luer fitting 40 that is preferably a ¼"-28 thread adapter Cole-Parmer Part No. E-30504-35. The female Luer fitting 40 includes a female coupling portion 42, a threaded cylindrical portion 44 and a central fixed engagement nut 46 with an axial bore 47 passing therethrough. The threaded cylindrical portion 44 of the Luer fitting 40 is threadably received within a threaded bore 48 of a planar circular retaining disk 50. The retaining disk 50 is preferably made from polyethylene, polycarbonate or other suitable material that may be sterilized by gamma radiation or other sterilization methods. The retaining disk 50 includes an annular groove 52 which is operable to removably and sealably retain the lip 24 of the first container 12. The second container 16 is preferably a syringe 16 such as VWR Scientific Part No. BD309604 or any other appropriate syringe 16 having a syringe barrel 54 and a plunger 56. The syringe 16 includes a male Luer fitting 58 positioned at a distal end 60 of the syringe barrel 54 and a finger flange or grip 62 positioned at a proximal end 64 of the syringe barrel 54. The plunger 56 includes a plunger thumb button 66, a plunger shaft 68 and a plunger seal 70.

Referring now to FIG. 2, the method of using the apparatus 10 for packaging, mixing and delivering bone cement will now be described in further detail. The apparatus 10 is preferably supplied as a complete assembly with the first container 12 being prepackaged with the first component 18 of the bone cement and the second container 16 being prepackaged with the second component 20 of the bone cement. The first component 18 is generally a granular or powder based component and the second component 20 is generally a liquid or fluid component. The first container 12 is selectively coupled to the closure mechanism 14, via the female and male Luer fittings 42 and 38, respectively. The second container 16 is selectively coupled to the closure mechanism 14, via the male and female Luer fittings 58 and 28, respectively, and the closure mechanism 14 is positioned in a first closed position, as shown in FIG. 2. The apparatus 10 is further constructed of materials which permits the entire apparatus 10 to be sterilized by various methods, such as by gamma radiation, prior to sealably packaging the entire apparatus 10 within a sterilized package.

During surgery, the sterilized apparatus 10 is first removed from its sterile package. Once removed, the handle 34 of the valve mechanism 26 is rotated in the first counterclockwise direction 35 from the first closed position, shown in FIG. 2, to a second open position, such that the handle 34 and the orifice 36 are axially aligned along the apparatus 10. This action selectively opens the first container 12 in order to receive the second component 20 of the bone cement from the second container 16. With the valve mechanism 26 open, the plunger button 66 of the plunger 56 is depressed in a first downward direction, identified by arrow 71, thereby injecting the second liquid component 20 through the closure mechanism 14 and into the first container 12. Once the plunger 56 is fully depressed, the handle 34 of the valve mechanism 26 is again rotated one-quarter turn in the second clockwise direction, thereby selectively closing the first container 12. The first and second components 18 and 20 which react to form the bone cement are then mixed substantially within only the first container 12 upon massaging or agitating the mixing member or flexible wall 22 of the first container 12.

Upon thoroughly mixing the first and second components 18 and 20 within the first container 12, the first container 12 may either be selectively disconnected from the closure mechanism 14, via the female and male Luer fittings 42 and 38, respectively. This opens and enables the first container 12 to either deliver the bone cement directly to the surgical site through the bore 47 passing through the Luer fitting 40 or to a spatula or other like device for subsequent delivery to the surgical site. Alternatively, the handle 34 may again be rotated in the first counter-clockwise direction 35 from its first closed position to its second open position. The bone cement is then drawn into the syringe barrel 54 of the second container 16 by simultaneously pulling the plunger 56 in a second upward direction opposite the downward direction 71, and squeezing the first container 12. This action draws and forces the bone cement into the syringe barrel 54 of the second container 16 due to the vacuum created within the syringe barrel 54.

The second container 16 may then be selectively disconnected from the closure mechanism 14, via the male and female Luer fitting 58 and 28, respectively. A hypodermic needle having a female Luer fitting may then be selectively coupled to the male Luer fitting 58 at the distal end 60 of the syringe barrel 54. This enables the second container 16 to deliver the bone cement directly to the desired surgical site without the need for using additional instruments to transport the bone cement to the surgical site. The bone cement may also be simply injected out of the distal end 60 of the syringe barrel 54 without the use of a hypodermic needle. The apparatus 10 therefore provides a convenient method for packaging, mixing and delivering a two-part bone cement in a timely manner without the possibility of contaminating the bone cement due to exposing the first and second components 18 and 20 to the environment.

Figures 4, 5, 6, 7:
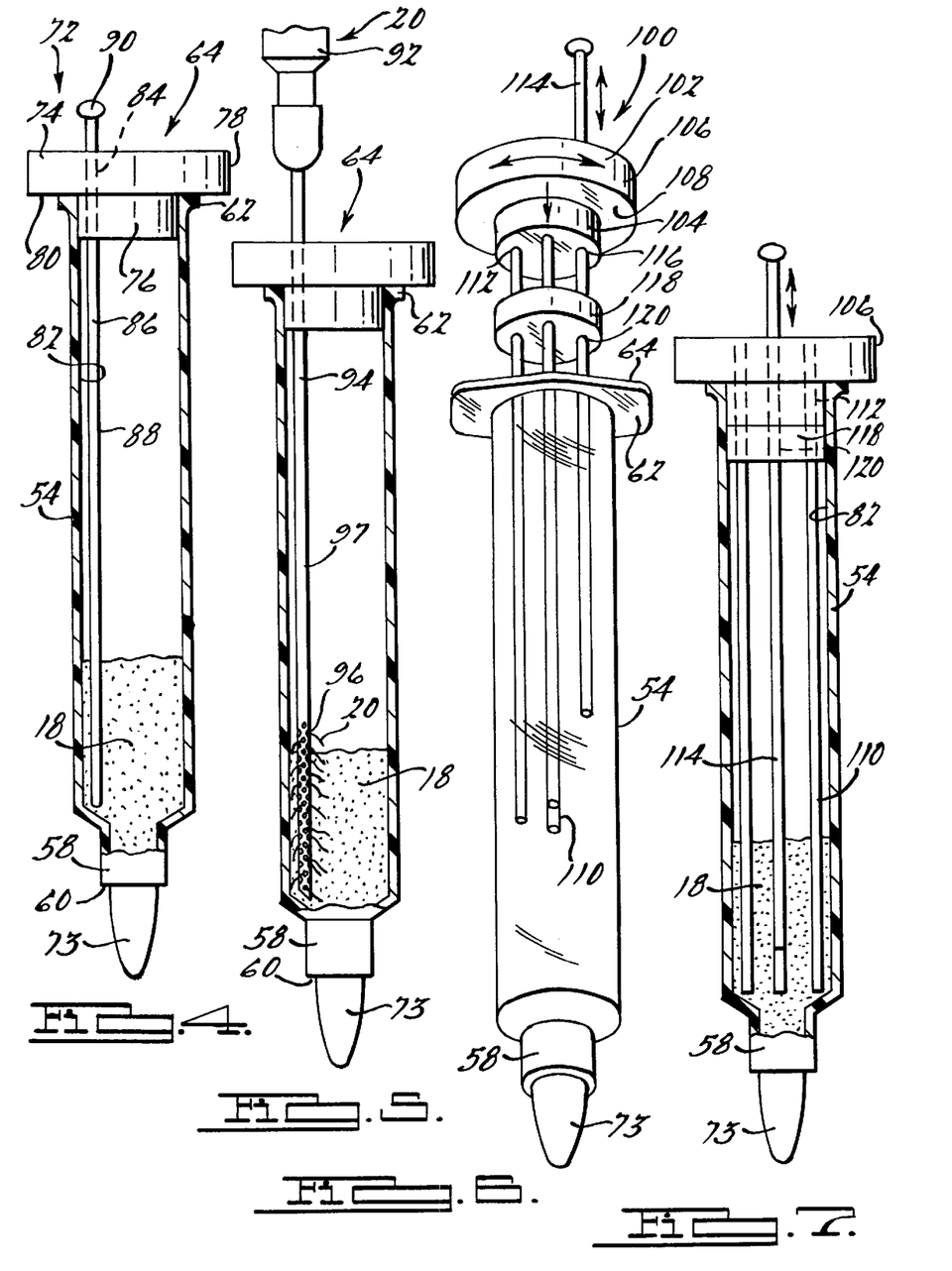
FIG. 4 is an assembled side cross-sectional view of the apparatus of FIG. 3 shown in use with a mixing rod.
FIG. 5 is an assembled side cross-sectional view of the apparatus of FIG. 3 shown in use with an irrigation hypodermic needle.
FIG. 6 is an exploded perspective view of an apparatus for packaging, mixing and delivering bone cement according to the teachings of a third preferred embodiment of the present invention.
FIG. 7 is an assembled side cross-sectional view of the apparatus of FIG. 6 shown in use with mixing rods.

Turning to FIGS. 3–5, a second preferred embodiment of an apparatus 72 for packaging, mixing and delivering bone cement is shown. In this regard, like reference numerals will be used to identify like elements as set forth in the first preferred embodiment. The apparatus 72 includes the syringe barrel 54 having the male Luer fitting 58 at the distal end 60 and the finger grip 62 at the proximal end 64. Located at the distal end 60 and removably coupled to the Luer fitting 58 is a conventional end cap 73 which is threadably received by the Luer fitting 58. Located adjacent to the proximal end 64 of the syringe barrel 54 is a cylindrical end cap 74. The end cap 74 includes a first cylindrical sidewall 76 having a first diameter and a second cylindrical sidewall 78 having a second larger diameter and an annular shoulder 80 formed therebetween. The first cylindrical sidewall 76 is operable to be sealably and rotatably received within an inner sidewall 82 of the syringe barrel 54. The annular shoulder 80 rotatably rides atop the proximal end 64 to prevent the end cap 74 from being fully received within the syringe barrel 54.

The end cap 74 further defines a bore 84 passing through the end cap 74 along a longitudinal axis offset from the center longitudinal axis of the end cap 74. A solid cylindrical mixing rod 86 is slidably and sealably received within the bore 84. The mixing rod 86 includes a cylindrical sidewall 88 and an enlarged end 90 to prevent the mixing rod 86 from falling into the syringe barrel 54. The end cap 74 is preferably made from a plastic and the mixing rod is preferably made from a rigid metal, both of which are capable of being sterilized.

The method for using the apparatus 72 first includes packaging the first container or syringe barrel 54 in a sterile package after prepackaging the syringe barrel 54 with the first component 18 of the bone cement. With the premeasured amount of the first component 18 being prepackaged in the first container 54, the sidewall 76 of the end cap 74 is sealably inserted within the sidewall 82 and the mixing rod 86 is slidably and sealably inserted within the bore 84 to selectively close and seal the proximal end 64 of the first container 54. When it is desired to use the bone cement, the sterile package is opened and the mixing rod 86 is slidably removed from the bore 84 by grasping the enlarged end 90 of the mixing rod 86 and removing it from the bore 84.

With the mixing rod 86 removed, a second syringe or container 92 prepackaged with the second component 20 is used to inject and deliver the second component 20 into the first container 54, via a hypodermic needle 94. It should be noted that the second container 92 may be packaged in the same sterile package as the first container. The hypodermic needle 94 preferably includes a plurality of irrigation holes 96 positioned along the sidewall 97 of the hypodermic needle 94, or simply a single irrigation hole. The second component 20 is injected into the first component 18, via the plurality of holes 96, to achieve a uniform disbursement of the second component 20 within the first component 18. Once the second component 20 has been injected into the first container 54, the hypodermic needle 94 is slidably removed from the bore 84 passing through the end cap 74. The mixing rod 86 is once again slidably and sealably received within the bore 84, similar to that shown in FIG. 4.

Once the mixing rod 86 is inserted within the syringe barrel 54, the second cylindrical sidewall 78 is grasped by a user and axially rotated both clockwise and counter-clockwise, thereby sealably rotating the first cylindrical sidewall 76 within the inner sidewall 82, as the mixing rod 86 rotates annularly within the syringe barrel 54 substantially adjacent to the sidewall 82. The rotating action of the mixing rod 86 thoroughly mixes both the first and second components 18 and 20 to form the bone cement. Once formed, the mixing rod 86 is slidably removed from the end cap 74 in order to remove any bone cement that may have adhered to the mixing rod 86. The end cap 74 is then removed and the plunger 56 is slidably inserted into the syringe barrel 54. The end cap 73 is then removed from the distal end 60 and a hypodermic needle may be threadably coupled to the Luer fitting 58. The plunger button 66 of the plunger 56 is then depressed to deliver or inject the bone cement to the desired surgical site.

Referring now to FIGS. 6 and 7, a third preferred embodiment of an apparatus 100 for packaging, mixing and delivering bone cement is shown. In this regard, like reference numerals will be used to identify similar structures as described with respect to the first and second preferred embodiments of the present invention. The apparatus 100 also uses the syringe barrel 54 having the Luer fitting 58 at the distal end 60 and the finger grip 62 at the proximal end 64. The end cap 73 is also removably coupled to the Luer fitting 58 at the distal end 60. The apparatus 100 is similar to the apparatus 72 except that it includes four mixing rods. Specifically the apparatus 100 includes an end cap 102 having a first cylindrical sidewall 104, a second cylindrical sidewall 106 and an annular shoulder 108 defined therebetween. Three mixing rods, identified by reference numeral 110, are fixedly secured to the end cap 102 within bores 112. A fourth cylindrical mixing rod 114 is slidably received within a bore 116 of end cap 102 similar to mixing rod 86. A wiping disk 118 slidably passes through mixing rods 110 and mixing rod 114, via bores 120. The wiping disk 118 includes a cylindrical sidewall 122 having a diameter which is substantially similar to the diameter of the first cylindrical sidewall 104.

In use, the syringe barrel or first container 54 is prepackaged with the first component 18. The end cap 102 is sealably fitted to the proximal end 64 of the first container 54 with the mixing rods 110 firmly secured thereto and the mixing rod 114 sealably extending through the bore 116. The end cap 73 is also coupled to the Luer fitting 58, thereby providing a substantially sealed first container 54. The first container 54 is sterilized and put into a sterile package either alone or with other instruments such as the second container 92. Once it is desired to mix the bone cement, the sterile package is opened and the mixing rod 114 is slidably removed from the bore 116. The hypodermic needle 94 is then passed through bore 116 to deliver the second component 20 from the second syringe or container 92 into the first container 54. Once the second component 20 has been injected into the first component 18, the hypodermic needle 94 is slidably removed from the bore 116 and the mixing rod 114 is again slidably and sealably received through the bore 116, again sealing the first container 54. The end cap 102 is again rotated similar to the end cap 74 such that the four mixing rods 110 and 114 are used to mix the first and second components 18 and 20, thereby reducing the mixing time, while providing a thorough mixing of the first and second components 18 and 20 within the first container 54.

Once mixed, the mixing rod 114 is slidably removed from the bore 120 of the wiper disk 118 and the bore 116 of the end cap 102, thereby removing any bone cement which is stuck to the mixing rod 114 as it is slidably passed through the bores 120 and 116. With the mixing rod 114 removed, the first cylindrical sidewall 104 is slidably removed from the inner sidewall 82 and held adjacent to the proximal end 64 of the syringe barrel 54 until a user grasps the wiper disk 118 as it is removed from within the cylindrical sidewall 82. Once the wiper disk 118 is grasped adjacent to the proximal end 64 of the syringe barrel 54, the end cap 102 is slidably pulled away from the wiper disk 118 as the mixing rods 114 pass through bores 120. The wiper disk 118 slidably cleans and removes bone cement from the mixing rods 110 as they slidably pass through bores 120, thereby reducing any waste or potential for contamination of the completed bone cement. It should also be noted that the mixing rod 114 may also be removed with the mixing rods 110 should this be desired. With the end cap 102 and mixing rods 110 and 114 fully removed from the syringe barrel 54, the plunger 56 is again inserted into the syringe barrel 54. The bone cement is then delivered to the desired surgical location, via the distal end 60 of the syringe barrel or through a hypodermic needle attached to the Luer fitting 58.

Figures 8, 9, 10, 11:
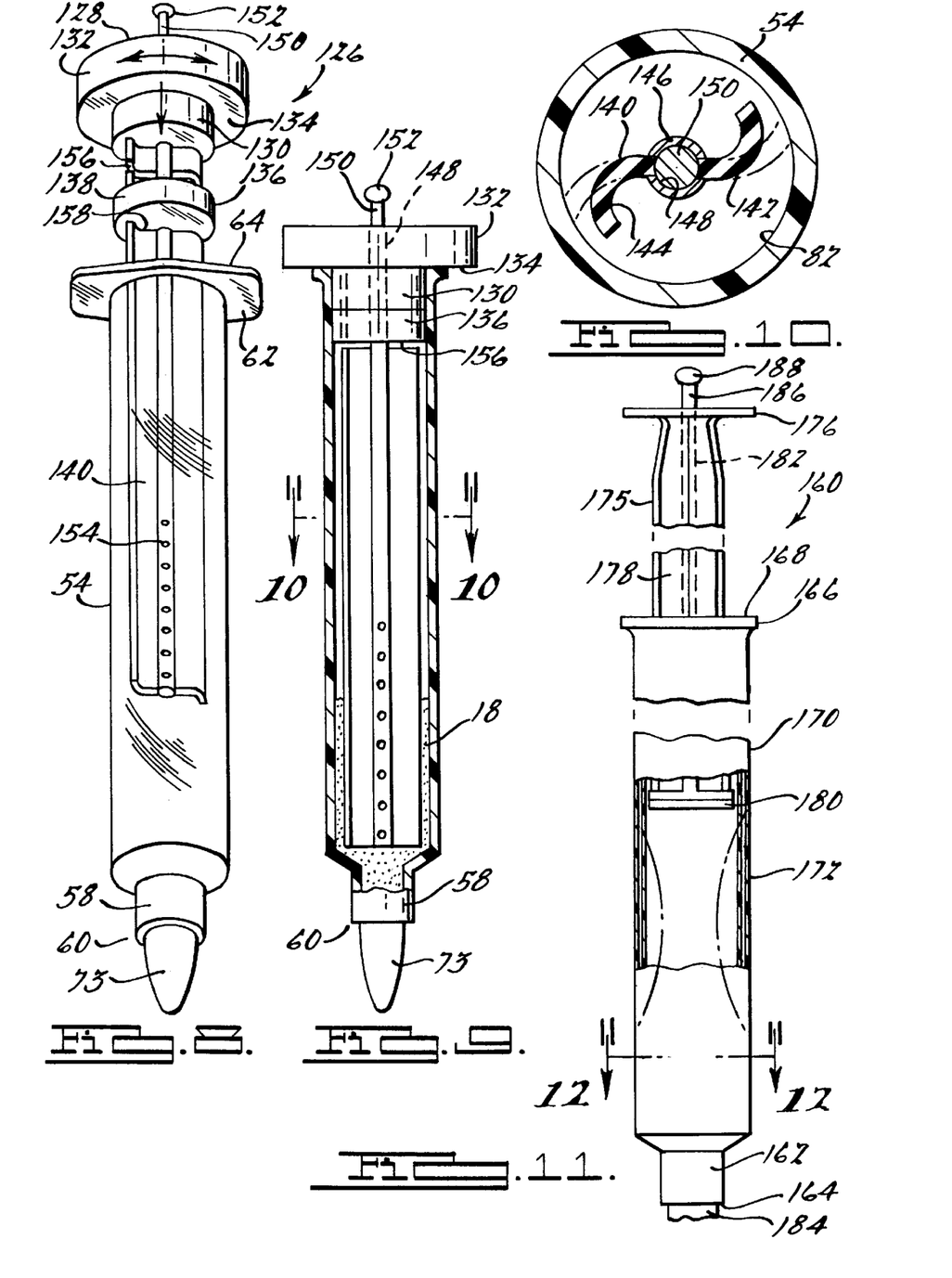
FIG. 8 is an exploded perspective view of an apparatus for packaging, mixing and delivering bone cement according to the teachings of a fourth preferred embodiment of the present invention.
FIG. 9 is an assembled side cross-sectional view of the apparatus shown in FIG. 8.
FIG. 10 is a lateral cross-sectional view of the apparatus shown in FIG. 8 taken along line 10—10 of FIG. 9.
FIG. 11 is a partial side cross-sectional view of an apparatus for packaging, mixing and delivering bone cement according to the teachings of a fifth preferred embodiment of the present invention.

Turning now FIGS. 8–9, a fourth preferred embodiment of an apparatus 126 for packaging, mixing and delivering bone cement is shown. In this regard, like reference numerals will be used to identify similar structures as used with respect to the other preferred embodiments. The apparatus 126 operates similar to the apparatus 72 and 100 and also employs the syringe barrel 54 having the Luer fitting 58 and end cap 73 at the distal end 60 and the finger grip 62 at the proximal end 64. The apparatus 126 further includes an end cap 128 having a first cylindrical sidewall 130, a second cylindrical sidewall 132 and an annular shoulder 134 formed therebetween. Positioned adjacent to the end cap 128 is a wiper disk 136 having a cylindrical sidewall 138 that is substantially the same diameter as the first cylindrical sidewall 130. Fixed to the end cap 128 is a mixing prop 140 having a first arcuate blade 142 and a second arcuate blade 144. The mixing prop 140 further includes a cylindrical axial body 146 defining an axial bore 148. The axial bore 148 passes axially through the mixing prop 140 and the end cap 128 such that the bore 148 is operable to receive a cylindrical rod 150 having an enlarged end 152 similar to the mixing rod 86 or 114. Irrigation holes 154 also pass laterally through the cylindrical body 146 and into the axial bore 148.

In use, the apparatus 126 is again packaged in a sterile container and prepackaged with the first component 18. The syringe barrel or first container 54 is selectively sealed with the end cap 128 and cylindrical rod 150 as the cylindrical sidewall 130 is slidably and sealably received within the inner sidewall 82 of the syringe barrel 54. When it is desired to mix the bone cement, the sterile package is opened and the cylindrical rod 150 is grasped at the enlarged end 152 and slidably removed from the axial bore 148. The hypodermic needle 94 having the plurality of irrigation holes 96 is then slidably received within the axial bore 148. It should be noted that a bore may also be formed offset the end cap 128 for receipt of a shorter hypodermic needle 94. The second container or syringe 92 injects the second component 20 from the hypodermic needle 94 into the first component 18 within the first container 54, via the holes 154. After the second component 20 is delivered to the first component 18, the hypodermic needle 94 is slidably removed from the axial bore 148 and the cylindrical rod 150 is again used to seal the axial bore 148.

The second cylindrical sidewall 132 is then grasped by a user and rotated both clockwise and counter clockwise to axially rotate the mixing prop 140 within the first container 54. Notches 156 formed within the arcuate blades 142 and 144 enable the blades 142 and 144 to flex freely without being inhibited by the wiper disk 136. Upon rotating the mixing prop 140 in a first clockwise direction, the first and second arcuate blades 142 and 144 flex inward along the axial center line of the mixing prop 140. Upon rotating the mixing prop 140 in a second counter-clockwise direction, the blades 142 and 144 are flexed outward, as shown in FIG. 10. As the blades 142 and 144 flex outwardly, the blades 142 and 144 scrap the inner sidewall 82 to provide further mixing of the first and second components 18 and 20.

Once the first and second components have been thoroughly mixed, the end cap 128 is slidably removed from the first container 54 and the wiper disk 136 is held adjacent to the proximal end 64. With the wiper disk 136 firmly held, the mixing prop 140 is slidably passed through an arcuate groove 158 formed within the wiper disk 136, thereby cleaning the mixing prop 140 as it slidably passes through the arcuate groove 158. The arcuate groove 158 is shaped to conform to the shape of the mixing prop 140 in its relaxed state so that the blades 142 and 144 align with the groove 158 when relaxed, via notches 156. Once removed, the plunger 56 is again inserted within the first container 54 to thereafter dispense the bone cement at the desired surgical site, via the distal end 60 or through a hypodermic needle attached to the male Luer fitting 58.

Figures 12, 13, 15, 16:
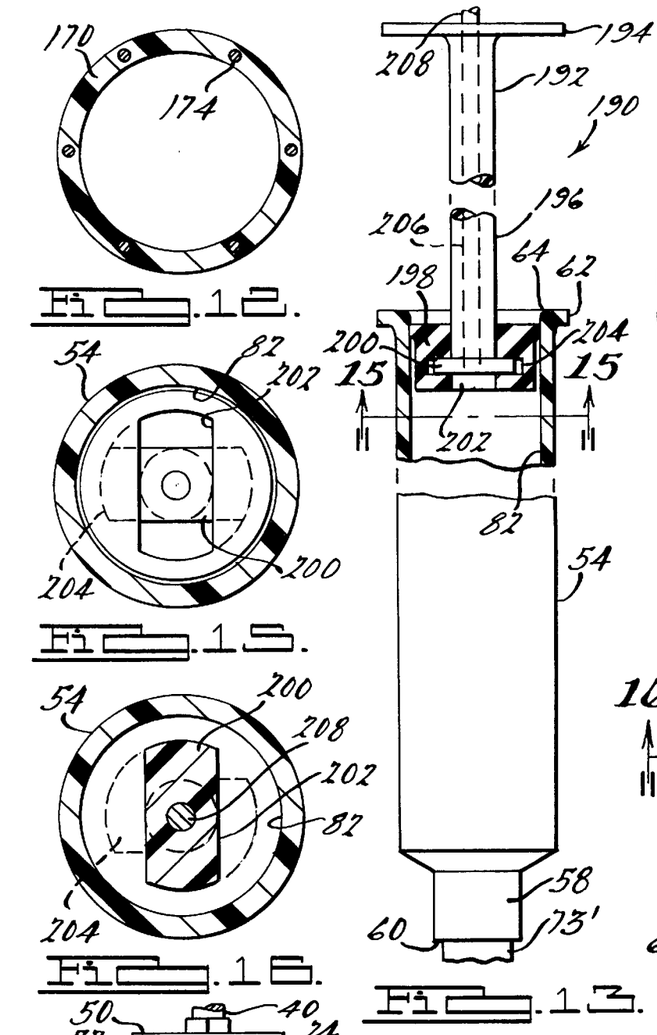
FIG. 12 is a lateral cross-sectional view of the apparatus shown in FIG. 11 taken along line 12—12 of FIG. 11.
FIG. 13 is a partial side cross-sectional view of an apparatus for packaging, mixing and delivering bone cement according to the teachings of a sixth preferred embodiment of the present invention shown with a plunger attached to a seal.
FIG. 15 is an end view of the plunger and seal taken along line 15—15 of FIG. 13.
FIG. 16 is an end view of the plunger and seal taken along line 16—16 of FIG. 14.

Turning now to FIGS. 11 and 12, an apparatus 160 for packaging, mixing and delivering bone cement according to a fifth preferred embodiment of the present invention is shown. In this regard, like reference numerals will be used to identify similar structures as used with respect to the previously described preferred embodiments of the present invention. The apparatus 160 is shaped substantially similar to the syringe 16, except that the apparatus 160 does not provide a rigid syringe barrel 54 but a flexible sidewall container. Specifically, the apparatus 160 includes a rigid female Luer fitting 162 at a distal end 164 of the apparatus 160 and a rigid finger grip 166 positioned at a proximal end 168 of the apparatus 160. The apparatus 160 further includes a first cylindrical container 170 having a flexible and resilient sidewall 172.

The flexible sidewall 172 is preferably made from a silastic tube that is capable of being massaged or compressed laterally and is reinforced longitudinally with flexible reinforcement rods or wire 174 formed within the sidewall 172. The reinforcement rods 174 may be coiled in the sidewall 172 or pass straight through the sidewall 172. Such reinforcement enables the sidewall 172 to be compressed and massaged laterally while reinforcing the sidewall 172 longitudinally, thereby enabling a plunger 175 to be slidably received within the cylindrical sidewall 172. The plunger 175 is substantially similar to the plunger 56 including having a plunger button 176, a plunger shaft 178 and a seal 180. Passing axially through the center of the shaft 178 is an axial bore 182. An end cap 184 is coupled to the distal end 164 and a cylindrical rod 186 having an enlarged end 188 is used to slidably seal bore 182.

In use, the first container 170 is prepackaged with the first component 18 and sealed with the end cap 184, plunger 175 and cylindrical rod 186. The entire assembly is again sterilized and sealed in a sterile package. Once it is desired to mix the bone cement, the sterile package is opened and the cylindrical rod 186 is slidably removed. The hypodermic needle 94 from the second container or syringe 92 is then inserted through the axial bore 182 to deliver the second component 20 into the first container 170. After the second component 20 is delivered to the first container 170, the hypodermic needle 94 is slidably removed from the axial bore 182 and the cylindrical rod 186 is again used to plug and seal the axial bore 182. The sidewall 172 of the first container 170 is then resiliently massaged and compressed laterally to mix the first component 18 and the second component 20 within the first container 170 as the sidewall 172 contracts and expands, as shown in FIG. 11. Once the first and second components 18 and 20 are thoroughly mixed to form the bone cement, the end cap 184 is removed and the bone cement is delivered to the surgical site upon compressing the plunger button 176 of the plunger 174.

Referring now to FIGS. 13–16, an apparatus 190 for packaging, mixing and delivering bone cement according to the teachings of a sixth preferred embodiment of the present invention is shown. In this regard, like reference numerals will be used to identify similar structures as described with respect to the previously described preferred embodiments. The apparatus 190 is substantially similar to the syringe 16 in that it includes the syringe barrel 54, having the Luer fitting 58 at the distal end 60, the finger grip 62 at the proximal end 64 and the end cap 73. The apparatus 190 further includes a modified plunger 192 having a plunger button 194, a plunger shaft 196, and a plunger seal 198. The plunger shaft 196 is detachably coupled to the seal 198, thereby enabling the plunger shaft 196 to act as a mixing member by slidably reciprocating the plunger shaft 196 within the seal 198.

Specifically, the plunger shaft 196 includes a T-shaped distal end 200 which is operable to be received within a groove 202 formed within the seal 198. With the end 200 passing through the groove 202, the T-shaped end 200 is then rotated within a chamber 204 about one-quarter of a turn in a first direction to thereby lock the end 200 within cavity 204. Once locked in place, the seal 198 of the plunger 192 axially moves along the inner sidewall 82 of the syringe barrel 54 along with the plunger 192. The plunger 192 further includes an axial bore 206 passing through the plunger 192, thereby providing access to the inside of the syringe barrel 54, via the hypodermic needle 94. The axial bore 206 is again sealed with a cylindrical rod 208 having an enlarged end 209.

Figure 14:
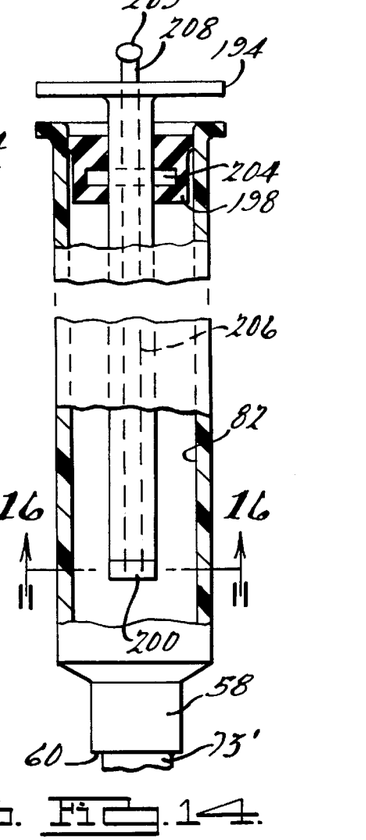
FIG. 14 is a partial side cross-sectional view of the apparatus of FIG. 13 shown with the plunger separated from the seal.

In use, the first container or syringe barrel 54 is again prepackaged with the first component 18 of the bone cement. The distal end 60 of the syringe barrel 54 is sealed by the end cap 73 and the proximal end 64 is sealed by the plunger 192 and the cylindrical rod 208. The entire assembly is again sterilized and placed in a sterile package, along with the second container 92, if desired. When it is desired to mix the bone cement, the sterile package is opened and the cylindrical rod 208 is slidably removed from the axial bore 206. The hypodermic needle 94 from the second container or syringe 92 is then slidably inserted into the bore 206. The second component 20 is delivered or injected into the first container or syringe barrel 54, via the holes 96, within the hypodermic needle 94. After the second component 20 is delivered to the first container 54, the hypodermic needle 94 is slidably removed from the axial bore 206 and the cylindrical rod 208 is again slidably received within the bore 206 to seal the bore 206.

The plunger 192 is then axially rotated in a second direction to align the T-shaped end 200 with the groove 202 in the seal 198. Once aligned, the plunger shaft 196 is slidably and sealably passed through the seal 198, as the seal 198 remains fixed along the sidewall 82 of the syringe barrel 54. Upon reciprocating the mixing member or plunger shaft 196, the first component 18 and the second component 20 are thoroughly mixed to form the bone cement. After being thoroughly mixed, the T-shaped end 200 is aligned with the groove 202 such that the chamber 204 of the seal 198 receives the T-shaped end 200. Once received, the plunger 192 is again rotated in the first direction to lock the T-shaped end 200 within cavity 204 of plunger 198. The bone cement is then delivered to the surgical site upon removing the cap 73 and compressing the plunger button 194 of the plunger 192, thereby slidably moving the seal 198 along the sidewall 82 to force the bone cement out of the distal end 60 and through a hypodermic needle if desired.

Figures 17, 18:
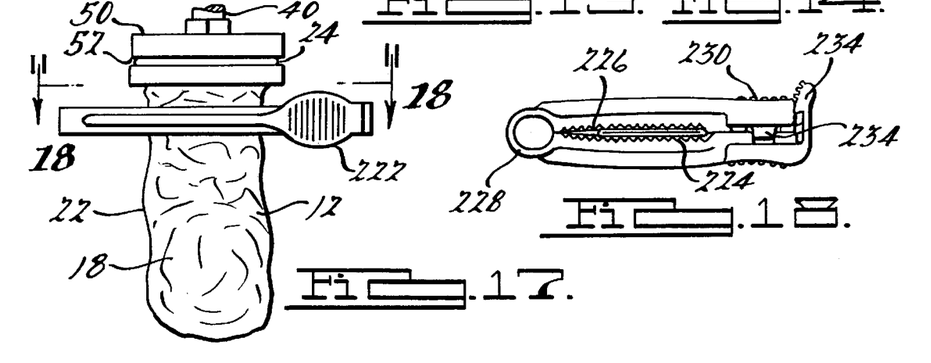
FIG. 17 is a side view of an apparatus for packaging, mixing and delivering bone cement according to the teachings of a seventh preferred embodiment of the present invention.
FIG. 18 is a side cross-sectional view of the clamp shown in FIG. 17 taken along line 18—18 of FIG. 17.

Referring finally to FIGS. 17 and 18, an apparatus 220 according to the teachings of a seventh preferred embodiment of the present invention is shown for packaging, mixing and delivering bone cement. In this regard, like reference numerals will be used to identify similar structures with regard to the first preferred embodiment of the present invention. The apparatus 220 includes the first container 12, the circular disk 50 and the male Luer fitting 40. In addition, the apparatus 220 further includes a clamp 222 which may be selectively locked and unlocked to open and close the first container 12. The clamp 222 includes a jaw 224 having mating teeth 226 which are hinged or pivoted about a flexible hinge 228, as shown clearly in FIG. 18. The clamp 222 further includes upper and lower finger grips 230, an alignment bar 232 and a resilient latch 234.

In use, the first container 12 having the flexible sidewall 22 is first prepackaged with the appropriate amount of the first component 18. The first component 12 is either filled, via the bore 47 in the Luer fitting 40 or through the top of the first container 12. If the first container 12 is filled directly, the rib 24 is then resiliently engaged about the annular groove 52 of the circular plate 50. Once the first container 12 is prepackaged, the first container 12 is selectively closed, via the clamp 222, to prevent the first component 18 from dispensing out the bore 47 in the Luer fitting 40. Again, the apparatus 220 is sterilized and sealed in a sterile package. In order to form the bone cement, the clamp 222 is selectively removed from the first container 12 by unlatching the resilient latch 234 to open the first container 12. The syringe 16 having the second component 20 prepackaged in the syringe 16 is then coupled to the lure fitting 40, via the male Luer fitting 58 of the syringe barrel 54. Once coupled, the button 66 of the plunger 56 is depressed to deliver the second component 20 within the first container 12. Once delivered, the syringe 16 is selectively removed from the Luer fitting 42 and the clamp 222 is again sealingly clamped about the container 12. Alternatively, a hypodermic needle may be coupled to the syringe 16 and used to deliver the second component 20 through the bore 37 in the Luer fitting 40. With the clamp 222 sealing the first container 12, the mixing member or flexible wall 22 of the first container 12 is used to resiliently massage and mix the first component 18 with the second component 20 to form the bone cement. After the bone cement is formed, the clamp 222 is again removed from the flexible container 12 and the bone cement is either delivered, via the bore 47 in the Luer fitting 40 or the syringe 16 is coupled to the Luer fitting 40 and the bone cement is drawn into the syringe or second container 16 for subsequent delivery to the desired surgical site.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. An apparatus for packaging, mixing and delivering bone cement formed from at least a first component and a second component, said apparatus comprising:

a first flexible bag operable to be selectively opened and closed, said first flexible bag having a flexible and resilient rib and being sealably prepackaged with the first component of the bone cement;

a second container operable to deliver the second component of the bone cement to said first bag; and a closure mechanism coupled to said first flexible bag by way of engaging an annular groove formed in a disk coupled to said closure mechanism with said flexible and resilient rib, said closure mechanism operable to selectively open and close said first flexible bag wherein upon opening said first flexible bag with said closure mechanism, said second container delivers the second component of the bone cement to said first bag, and wherein upon closing said first flexible bag with said closure mechanism, said first flexible bag is operable to mix the first and second components of the bone cement substantially within only said first flexible bag upon massaging said first flexible bag.

2. The apparatus as defined in claim 1 wherein said second container is a syringe prepackaged with the second component of the bone cement.

3. The apparatus as defined in claim 2 wherein said closure mechanism is a valve mechanism selectively coupled to said first flexible bag and selectively coupled to said second container wherein said first flexible bag and second container may be selectively coupled and removed from said valve mechanism.

4. A method for packaging, mixing and delivering bone cement formed from at least a first component and a second component, said method comprising the steps of:

providing a first container that is operable to be selectively opened and closed;

prepackaging the first container with the first component of the bone cement disposed therein;

coupling the first container to a valve body by engaging an annular groove formed in a disk coupled to the valve body with a flexible rib forming part of the first container;

selectively opening the first container;

delivering the second component of the bone cement from a second container to the first container;

selectively closing the first container; and mixing the first and second components of the bone cement substantially within only the first container with a mixing member forming part of the first container.

5. The method as defined in claim 4 wherein the step of providing a first container further comprises the step of providing a first flexible container having a flexible sidewall acting as said mixing member, wherein upon massaging the flexible sidewall, the first and second components of the bone cement are mixed within the first flexible container.

6. The method as defined in claim 4 wherein the step of selectively opening and closing the first container further includes the steps of rotating a closure member within the valve body to selectively open and close the first container.

7. A preassembled apparatus for packaging, mixing and delivering bone cement formed from at least a first component and a second component, said preassembled apparatus comprising:

a flexible bag operable to be selectively opened and closed, said flexible bag prepackaged with the first component of the bone cement;

a syringe having a syringe body and a plunger, said syringe prepackaged with the second component of the bone cement; and a valve mechanism operable to enable communication between said flexible bag and said syringe, said valve mechanism coupled to said flexible bag and said syringe, said valve mechanism inhibiting communication between said flexible bag and said syringe when in a first position and enabling communication between said flexible bag and said syringe when in a second position, wherein upon positioning said valve mechanism in said first position and depressing said plunger of said syringe, the second component of the bone cement is delivered to said flexible bag prepackaged with the first component of the bone cement.

8. The preassembled apparatus as defined in claim 7 wherein said flexible bag is coupled to said valve mechanism by way of engaging an annular groove formed in a disc coupled to said valve mechanism with a flexible rib forming a portion of said flexible bag.

9. The preassembled apparatus as defined in claim 7 wherein said syringe is coupled to said valve mechanism by way of mating Luer fittings extending from said syringe and said valve mechanism.

* * * * *

UNITED STATES PATENT AND TRADEMARK OFFICE
CERTIFICATE OF CORRECTION

PATENT NO. : 5,951,160
DATED : September 14, 1999
INVENTOR(S) : Robert Ronk

It is certified that error appears in the above-identified patent and that said Letters Patent is hereby corrected as shown below:

Column 7,
Line 63, after "now" insert -- to --.

Column 8,
Line 51, delete "scrap" and substitute -- scrape -- therefor.

Signed and Sealed this

Fifth Day of March, 2002

Attest:

JAMES E. ROGAN
Attesting Officer    Director of the United States Patent and Trademark Office